United States Patent
Tran-Thi et al.

(10) Patent No.: US 9,841,410 B2
(45) Date of Patent: Dec. 12, 2017

(54) LIQUID PHASE PHENOL ANALYSIS

(71) Applicants: COMMISSARIAT A L'ENERGIE ATOMIQUE ET AUX ENERGIES ALTERVATIVES, Paris (FR); CENTRE NATIONAL DE LA RECHERCHE SCIENTIFIQUE—CNRS, Paris (FR)

(72) Inventors: Thu-Hoa Tran-Thi, Montrouge (FR); Laurent Mugherli, Vaugrigneuse (FR); Ana Borta, Palaiseau (FR)

(73) Assignees: COMMISSARIAT A L'ENERGIE ATOMIQUE ET AUX ENERGIES ALTERNATIVES, Paris (FR); CENTRE NATIONAL DE LA RECHERCHE SCIENTIFIQUE—CNRS, Paris (FR)

( * ) Notice: Subject to any disclaimer, the term of this patent is extended or adjusted under 35 U.S.C. 154(b) by 0 days.

(21) Appl. No.: 14/994,171

(22) Filed: Jan. 13, 2016

(65) Prior Publication Data
US 2016/0202220 A1   Jul. 14, 2016

(30) Foreign Application Priority Data
Jan. 13, 2015  (FR) ...................................... 15 50243

(51) Int. Cl.
| | |
|---|---|
| *G01N 15/06* | (2006.01) |
| *G01N 21/00* | (2006.01) |
| *G01N 1/18* | (2006.01) |
| *G01N 31/22* | (2006.01) |
| *B01D 53/72* | (2006.01) |
| *C02F 1/72* | (2006.01) |

(Continued)

(52) U.S. Cl.
CPC .......... *G01N 31/224* (2013.01); *B01D 53/72* (2013.01); *C02F 1/72* (2013.01); *G01N 21/78* (2013.01); *G01N 21/783* (2013.01); *G01N 31/22* (2013.01); *G01N 33/22* (2013.01); *C02F 2101/345* (2013.01)

(58) Field of Classification Search
CPC .......... G01N 15/06; G01N 21/00; G01N 1/18
USPC ................. 422/68.1, 430, 83, 85, 86, 82.05; 436/178, 131
See application file for complete search history.

(56) References Cited

U.S. PATENT DOCUMENTS

| | | | |
|---|---|---|---|
| 4,916,058 A | 4/1990 | Aoyama et al. | |
| 5,215,885 A * | 6/1993 | Marrujo | C12Q 1/28 435/188 |

(Continued)

FOREIGN PATENT DOCUMENTS

| | | |
|---|---|---|
| CN | 102590198 A | 7/2012 |
| CN | 202362242 U | 8/2012 |

(Continued)

*Primary Examiner* — Brian J Sines
(74) *Attorney, Agent, or Firm* — Young & Thompson (57) ABSTRACT

A liquid reagent composition for detecting phenol or phenol derivatives includes a reagent capable of generating a stained product by forming a bond with phenol, an oxidant compound or mixture of oxidant compounds, a basic compound or mixture of basic compounds. The ratio of [stained reagent]:[oxidant compound] is 1:2 to 50:1, having a pH greater than 7. Also disclosed is a kit for the use of the composition and liquid-phase method for analysing a fluid potentially containing phenol or a phenol derivatives.

9 Claims, 4 Drawing Sheets

(51) Int. Cl.
*G01N 21/78* (2006.01)
*G01N 33/22* (2006.01)
*C02F 101/34* (2006.01)

(56) References Cited

U.S. PATENT DOCUMENTS

| | | | | |
|---|---|---|---|---|
| 5,219,762 | A * | 6/1993 | Katamine | A61B 10/0035 |
| | | | | 422/504 |
| 2005/0214161 | A1* | 9/2005 | Gupta | G01N 33/5091 |
| | | | | 422/400 |
| 2008/0233654 | A1* | 9/2008 | Green | C01C 1/086 |
| | | | | 436/56 |
| 2013/0280817 | A1 | 10/2013 | Tran-Thi et al. | |
| 2013/0337481 | A1* | 12/2013 | Eckersall | C12Q 1/28 |
| | | | | 435/14 |
| 2015/0276646 | A1* | 10/2015 | Kawde | G01N 27/48 |
| | | | | 205/782 |
| 2016/0202221 | A1* | 7/2016 | Tran-Thi | G01N 31/224 |
| | | | | 436/131 |

FOREIGN PATENT DOCUMENTS

| WO | 2012/080665 A1 | 6/2012 |
|---|---|---|
| WO | 2014/160212 A1 | 10/2014 |

\* cited by examiner

LIQUID PHASE PHENOL ANALYSIS

The present invention relates to a reagent composition and a method for analysing phenol or phenol derivatives in liquid phase and the applications thereof.

Phenol and its derivatives are highly toxic compounds. They are widely used in the production or manufacture of a large variety of aromatic compounds including explosives, fertilisers, lighting gases, paints, rubber, textiles, pharmaceutical products, perfumes and plastics, such as for example polycarbonates or epoxy resins. Phenol is routinely used as an intermediate in synthetic industrial chemical processes and notably in the petroleum, plastics, dye, leather, paper, soap industries. To a lesser degree, phenol and its derivatives are used in the composition of cosmetics and medicinal products. In some countries, phenol is also used as a mosquito repellent and as an insecticide and weed killer for agriculture. Consequently, phenol and its derivatives are found in the environment mostly via industrial emissions, but also via domestic activity (human and animal metabolism, waste water, household fuel oil combustion). Traces of phenol are also present in motor vehicle exhaust gases or tobacco smoke. Since 2006, the use of phenol as a disinfectant has been prohibited in France. However, phenol derivatives, such as chlorophenols for example, are frequently used as a substitute. As such, phenol and its derivatives are omnipresent, in air and in water, at variable concentrations according to human activity.

Phenol is toxic by inhalation, in contact with skin and if swallowed. It is also liable to induce genetic abnormalities. In the event of contact, it causes skin burns and eye lesions. Repeated or prolonged exposure may induce severe effects for organs, such as: digestive disorders, headaches, salivation, anorexia, vomiting and loss of appetite. It also causes bone marrow damage.

The restrictive occupational exposure limits for air in work premises have been set in France and in the European Union to 2 ppm (7.8 mg/m$^3$) for a weighted average over 8 hours and to 4 ppm (15.6 mg/m$^3$) for short-term exposure of not more than 15 min (as per the toxicology file of the French National Institute for Research and Health—INRS).

At the present time, sensitive, selective and reliable detection of phenol in a gas mixture is performed using an indirect method with gas sampling and subsequent analysis in a laboratory.

In order to detect phenol in solution, it is necessary to use a different method, the reference being the colorimetric method based on 4-aminoantipyrine (AAP), wherein phenol cannot be added last, and the reagents, previously stored separately, must be added at the last minute, which renders the method very complex. Finally, these methods can only be used for detection, and under no circumstances for depollution, if the presence of phenol is established.

There are numerous methods for detecting phenol in aqueous solution or in the air.

The detection methods are essentially broken down into three categories: chromatographic methods, electrochemical methods and colorimetric methods. Further methods also exist and are under development such as for example methods based on mass microvariation (piezoelectric resonators).

Chromatographic methods require costly apparatuses and complex procedures. In addition, they induce a response time when they are used indirectly (field sampling following laboratory analysis).

Electrochemical methods are not readily adaptable for detection in air and frequently require the addition of modified electrodes containing nanoparticles, polymers or enzymes. The costs of such electrodes and the ageing thereof under actual conditions of use may constitute an impediment to the industrialisation thereof.

Chromatographic and electrochemical methods exhibit intrinsic complexity either in the raw material (enzymes, nanoparticles, etc.), in the preparation (materials), in the operating protocol thereof (sampling, extraction, concentration, purification, addition of other reagents, assay), or in the measurement per se (complex, bulky apparatuses). With this complexity, a relatively high cost and a potentially long time to obtain results are thus associated. Furthermore, a certain expertise is required to run the samples and interpret the results, as these methods are far from being simple to use.

Colorimetric methods have the advantage of being simpler to use in terms of preparation, sampling, measurement, and obtaining results. These methods are generally direct (no retrospective laboratory analysis). The response is thus quicker. Furthermore, the apparatus required is inexpensive, and more compact.

In the literature, there are a large number of colorimetric methods for detecting phenol or its derivatives in solution, using reagents in an acid medium, such as p-diazobenzenesulphonic acid (DABS) which gives rise to a yellow colour, the mixture Fe(II)/1,10-phenanthroline which produces pink staining, the mixture formaldehyde-sulphuric acid (FSA) and the purple staining thereof, or iodine bromide which forms an absorbent product in the UV range. Reactions in basic medium have also been described, using for example Folin-Ciocalteu's reagent, which develops blue staining. Further reagents require extraction with an organic solvent of the stained product, such as for example the brown product of Millon's reagent, the pink product of MBTH (3-Methyl-2-benzothiazolinone hydrazone hydrochloride monohydrate) in the presence of an oxidant, or the blue load transfer complexes derived from 2,3-dichloro-5,6-dicyano-p-benzoquinone (DDQ). Some of these reagents are costly, others toxic. Furthermore, they may require an extraction step before the colour analysis. They are not all sufficiently sensitive and selective.

The most commonly used method which provides satisfactory sensitivity and selectivity, probably because it is the simplest, is based on the use of 4-aminoantipyrine (AAP). Moreover, it is the reference method cited by the French National Institute for the Industrial Environment and Risks (INERIS). The method involves the formation of a quinoid complex between 4-aminoantipyrine and phenol in a basic medium (preferentially pH=9 or 10) and in the presence of the oxidant potassium hexacyanoferrate. Staining develops after 5 min for concentrations greater than 1 mg/L i.e. approximately 10 μM (193 ppb) and the quinoid compound has an absorption peak around 510 nm. It should be noted that for concentrations below 1 mg/L, INERIS recommends three successive extractions with chloroform, which renders the operation notably more complex. In the literature, this reaction is described with various AAP compounds and various oxidants, and with various [AAP]:[oxidant] ratios, for example Analytical Chimica Acta, 467, 2002, 105-114, Jour. Chem. Soc. Pak., 27, 2005, 271-274, or Jour. Organ. Chem., 8, 1943, 417-428.

The AAP compounds mentioned in some publications are of interest, notably those making it possible to increase sensitivity by means of a higher molar extinction coefficient. However, they are not easy to acquire as they are mostly synthesised on commission. The majority of methods based on AAP described in the literature enable selective and sensitive detection of the order of a few ppb, but they all use a chloroform extraction step which complicates the protocol and prolongs the duration thereof. If seeking to do away with this extraction step, the INRS guidelines and rare publications with direct detection in aqueous solution indicate a significant drop in sensitivity: the method only works correctly for concentrations greater than 200 ppb (1mg/L, 10 µM). All these methods use excess oxidant, and the order of use of the reagents is always the same, i.e.: 1) buffer solution, 2) phenol, 3) AAP, 4) oxidant. The waiting time before measuring the absorbance varies from 5 to 30 min.

Attempts to adapt this reference phase in liquid phase to the detection of phenol in gas phase are not convincing. Indeed, only two patents have been filed, and adaptation required a significant complication of the method [Patents CN102590198 and CN202362242U]. A plurality of steps are added, notably dissolution in acid medium, distillation, stripping, heating, extraction. Furthermore, in one of the patents, the reagents are added sequentially, which complicates the method further [Patent CN202362242U].

The disclosure above demonstrates that, at the present time, there is no simple and direct colorimetric method based on the use of AAP or the compounds thereof, which is selective and sensitive, and which enables the detection of phenol in solution by adding same last, in other words, there is no method where the addition of the sample constitutes the final step.

The methods developed for the detection of phenol in air are much less numerous. By an overwhelming majority, known methods are performed in a plurality of steps. Firstly, sampling of air containing phenol is performed via a tube filled with silica gel or resin (typically XAD7), and this sampling is then followed by desorption with solvents and derivatisation with a silylation agent, then, an assay is performed, by gas chromatography with flame ionisation detection or by liquid chromatography with UV or electrochemical detection.

The only direct method, i.e. with no retrospective laboratory analysis, consists of using GASTEC (No. 60) or DRAEGER (Phenol 1/b, MSA Phenol-1) graduated tubes. The detection principle is based on reacting phenol in an acid medium with $(NH_4)_2Ce(NO_3)_6$ (for GASTEC) and $Ce(SO_4)_2$ (for DRAEGER), which produces a change of colour from yellow to brown-green. The stained product spreads through the tube with a rate dependent on the phenol concentration for a gas stream pumped at a flow rate defined by the manufacturer. The concentration reading is performed using the graduations printed on the tube. The most effective is the GASTEC tube, with a detection range of 0.4 to 187 ppm with an error of 10% to 15% indicated by the manufacturer. The advantage of this detection is the simplicity thereof, but the detection reaction is not selective, and it is necessary to apply a correction factor based on the humidity and the temperature. As such, these tubes do not provide the selectivity or the precision required for comparison with an occupational exposure limit value as per INRS. These tubes cannot be used in water, which represents a further limitation with the method.

Therefore, at the present time, there is no direct, selective and sensitive colorimetric method suitable for detecting phenol or phenol derivatives in liquid phase. Furthermore, no universal method for the detection both in a fluid such as a gas mixture such as air or in a solution, for example aqueous, by merely contacting a ready-to-use composition with the fluid, has been developed to date.

It would thus be desirable to have such a method. The method should enable direct, optical or visual detection feasible in the field with portable equipment, to prevent the transport of samples to be tested to a laboratory equipped to make such a measurement. The method should also be simple. It should be suitable for use equally well for the detection of phenol in a gaseous or liquid mixture. The method should be suitable not only for use for detection, but also if possible for selective depollution of phenol and its derivatives.

The present invention makes it possible to solve all or some of the technical problems associated with the detection of phenol mentioned above.

After long research, the inventors have developed a method inspired by the colorimetric reaction in solution based on AAP, but with major changes, which have resulted in a precise and reliable, but considerably simplified, method.

With the reference method, the oxidant is always used in excess and the order of addition of the reagents is very important: 1) buffer solution, 2) phenol, 3) AAP, 4) oxidant. In the presence of excess oxidant, if this order is not observed, the change of colour does not occur. For simple use, the applicant envisaged placing all the pre-mixed reagents in the presence of phenol and not having any other operation to be performed subsequently, apart from reading the measurement result. As such, the phenol (or phenol derivative) would necessarily be contacted with the other reagents last.

The present invention is based on a pre-mixed reagent mixture using two innovations: modification of the order of addition of the reagents and modification of the [AAP]: [potassium hexacyanoferrate] ratio. Pre-mixing reagents makes it possible to detect phenol directly by contacting the fluid potentially containing phenol with a reagent composition according to the invention, for example by mere bubbling in the case of a gaseous fluid.

For this reason, the present invention relates to a liquid reagent composition for the detection of phenol or phenol derivatives characterized in that it comprises:

a reagent capable of generating a stained product by forming a bond with phenol,
an oxidant compound or mixture of oxidant compounds,
a basic compound or mixture of basic compounds,
in that the ratio of [reagent capable of generating a stained product]:[oxidant product] is 1:2 to 50:1,
and in that it has a pH greater than 7.

Within the scope of the present invention, the reagent capable of generating a stained product is a compound enabling a colour to be developed by forming a generally covalent bond with phenol or a phenol derivative, to form a coloured compound, for example a quinoid compound. The reagent capable of generating a stained product is preferably AAP but may also be an AAP derivative, such as for example a compound corresponding to formula I formula I where: R1 is an alkyl radical containing 1 to 30, notably 1 to 12, preferentially 1 to 6 carbon atoms, linear or branched, or an aryl radical, preferably phenyl, preferentially a radical $C_6H_5$, $CH_3$ or $C_2H_5$; R2 is a phenyl or para-aminophenyl radical, preferentially the latter; R3 is an alkyl radical containing 1 to 30, notably 1 to 12, preferentially 1 to 6 carbon atoms, linear or branched, or optionally substituted phenyl, preferably in the para position, for example by an amino or halogen radical, such as a para-aminophenyl or parachlorophenyl radical. The reagent capable of generating a stained product is preferably AAP.

The liquid reagent composition according to the invention also contains an oxidant compound or mixture of oxidant compounds. The oxidant compound or oxidant compounds are advantageously chosen in the group consisting of potassium persulphate, potassium peroxomonosulphate; hydrogen peroxide or potassium hexacyanoferrate. The latter is advantageously used which enables a good compromise between smoothness of the oxidation and reaction rate. Oxidants other than those in the non-exhaustive list above are possible.

The liquid reagent composition according to the invention also contains a basic compound or mixture of basic compounds. Given that the reagent composition according to the invention is liquid, a buffer solution is advantageously used, such as for example a phosphate, 2-amino-2-(hydroxymethyl)-1,3-propanediol, carbonate, glycine-sodium hydroxide or borate buffer, preferentially a borate buffer, to obtain a basic pH equal to preferably approximately 10. The basic compound or mixture of basic compounds is necessary for the proper completion of the stained reaction, while adding the phenol or phenol derivative last.

Note that in the present application, conventionally the indefinite article "a" should be considered as a generic plural (meaning "at least one" or "one or a plurality"), unless demonstrated otherwise by the context (1 or "a single"). As such, for example, when it is said above that the liquid reagent composition according to the invention comprises a reagent capable of generating a stained product or comprises a basic compound, it should be understood that the liquid reagent composition contains one or a plurality of reagents capable of generating a stained product or basic compounds. Under preferential conditions of use of the invention, the reagent capable of generating a stained product is AAP, and the basic compound or mixture of basic compounds is chosen from among a phosphate buffer or a borate buffer, preferentially a borate buffer, and the oxidant compound or oxidant compounds is potassium hexacyanoferrate or a mixture of potassium hexacyanoferrate and one or a plurality of further oxidant compounds.

Excess reagent capable of generating a stained product, typically greater than 50:1, is not desirable as the staining stability is reduced, and the peak of the reagent capable of generating a stained product may interfere with the one of the stained product derived from the stained reaction.

The ratio of [reagent capable of generating a stained product]:[oxidant compound] is preferably 1:2 to 25:1, advantageously 1:2 to 20:1, notably 1:2 to 10:1, particularly 1:2 to 5:1, and more particularly 1:1.

In the liquid reagent composition according to the invention, the reagents may be present in quantities such that, after mixing, the concentrations of reagent capable of generating a stained product are equal to $1.0.10^{-1}$ M to $5.0.10^{-3}$ M, advantageously $1.0.10^{-2}$ M to $5.0.10^{-4}$ M, preferably $1.0.10^{-3}$ M to $5.10^{-5}$ M, notably $2.0.10^{-4}$ M to $1.0.10^{-5}$ M, more particularly $6.0.10^{-4}$ M to $4.0.10^{-5}$ M.

In the liquid reagent composition according to the invention, the reagents may be present in quantities such that, after mixing, the concentrations of oxidant are equal to: $2.0.10^{-1}$ M to $2.0.10^{-4}$ M, advantageously $2.0.10^{-2}$ M to $2.0.10^{-5}$ M, preferably $2.0.10^{-3}$ M to $2.10^{-6}$ M, notably $4.0.10^{-4}$ M to $4.0.10^{-7}$ M, more particularly $1.2.10^{-4}$ M to $8.0.10^{-5}$ M.

Preferentially, the reagent composition essentially consists of the above components, and more particularly consists of said components.

While, within the scope of the invention, a ready-to-use liquid reagent composition may be used, it is also possible to procure the various constituents separately, to prepare extemporaneously the mixture which may be used for the detection or assay of phenol or one of its derivatives.

For this reason, the present application also relates to a kit characterized in that it comprises separately
a reagent capable of generating a stained product,
an oxidant compound or mixture of oxidant compounds,
a basic compound or a mixture of basic compounds,
where the ratio of [reagent capable of generating a stained product]:[oxidant product] is 1:2 to 50:1.

While they may be added in solution, the reagent capable of generating a stained product, the basic compound or mixture of basic compounds, and the oxidant compound are preferably in solid form.

As such, it is simply necessary to place one of the constituents in solution, preferably the basic compound or mixture of basic compounds, and then mix all the constituents.

Under preferential conditions of use of the kit, the reagent capable of generating a stained product and the oxidant compound are in solid form, and the basic compound or mixture of basic compounds is in solution. The basic compound or mixture of basic compounds is preferentially borate buffer at pH 9.

The invention may in particular take the form of a detection kit comprising a basic solution and a container, preferentially protected from light. This container contains, in separate locations, advantageously in an inert atmosphere, the reagent capable of generating a stained product and the oxidant compound in solid form.

The container is preferably a closed container provided with zones (optical windows) enabling optical detection by a suitable apparatus, and openings for the circulation or addition of liquids or gases. As such, it is possible to add the basic solution to the solid constituents and mix all the reagents, to obtain a ready-to-use solution.

In one particular embodiment of the kit, the container is equipped with a removable separation providing two juxtaposed compartments wherein are placed in one, the reagent capable of generating a stained product and in the other the oxidant compound, in solid form, this mixture being suitable for being made by removing the removable separation.

The detection of phenol or a phenol derivative in a liquid fluid may be performed for example directly via the openings of the container. Bubbling a gas mixture containing phenol or a phenol derivative is possible directly in the container.

Detection may be performed directly by connecting an optical detection system to the optical windows of the container.

Under further preferential conditions of use of the kits according to the invention, a container comprises three compartments, the first two being equivalent to those above, and the third compartment being reserved for the basic compound or mixture of basic compounds in solid form, for example a mixture of borax and sodium hydroxide to reconstitute the pH 9 borate buffer.

It is indeed possible to prepare the buffer adjusted to the correct pH and freeze-dry same, but the quantity of solid corresponding to the buffer in the kit is then very low (of the order of one mg) and thus difficult to weigh. As the buffer is well preserved in solution; the benefit/complication ratio would in our view not be of interest. However, it is possible.

In order to carry out a detection or assay, it is simply necessary to add a solvent such as water and then mix. Such a kit has a particularly long shelf-life.

The above embodiments provide ready-to-use means in spectrophotometric measurement devices. However, those skilled in the art understand that it is not necessary for the container to have optical windows, and that it is thus possible, once the mixture has been made, to transfer same into a vessel suitable for spectrophotometric measurements.

The reagent composition according to the invention may be readily prepared by merely mixing different constituents, which themselves are readily available and inexpensive.

The present application also relates to a method for preparing a reagent composition above, characterized in that the various constituents are mixed according to methods known per se.

The present application also relates to a method for preparing a kit above, characterized in that the various constituents of the reagent are provided, for example in sachets, in bottles, or directly in a container preferably equipped with one or a plurality of separating partitions to avoid mixing the various constituents before use.

The reagent compositions and kits according to the present invention have very interesting properties. In the reagent compositions and kits above, a ready-to-use solution is obtained. If phenol or a phenol derivative is present or suspected in a liquid, it is sufficient to add a certain volume of liquid to the system. If it is present, the phenol or phenol derivative will then react with the reagents present in the container to form a coloured compound having an absorption peak. This absorbance property of the solution may be correlated with the concentration of phenol or phenol derivative by means of a calibration curve. With the absorbance is associated a change of colour of the solution visible to the naked eye. The detection may thus be qualitative or quantitative. For a gas or gas mixture, it is sufficient to bubble the gaseous fluid in the ready-to-use or extemporaneously prepared solution.

These properties are illustrated hereinafter in the experimental section. They justify the use of the reagent compositions and kits described above, in the analysis of a fluid potentially containing phenol or a phenol derivative.

For this reason, the present application also relates to a liquid phase method for analysing a fluid potentially containing a phenol or a phenol derivative characterized in that the fluid is contacted with a liquid reagent composition for detecting phenol or phenol derivatives defined above and in that any staining obtained is observed or measured.

The phenol derivatives are for example alkoxyphenols, nitrophenols, chlorophenols, or polyaromatic phenols. Particular mention may be made of 4-methoxyphenol, 2-nitrophenol, 2,4-dichlorophenol, or naphthol, but also cresol, catechol, resorcinol, 2,4-dimethylphenol, 4-chloro-3-methylphenol, 4-nitrophenol, 2,4-dinitrophenol, 4,6-dinitrophenol, 4-chlorophenol, 2-chlorophenol, 2,4,6-trichlorophenol, pentachlorophenol.

Under conditions of use of the method above, the fluid potentially containing phenol or a phenol derivative is a gas or a gas mixture. Under further conditions of use of the method above, the fluid is a liquid.

When the fluid is a liquid, this liquid is for example water, ethanol, THF or DMSO, preferentially in a mixture with water.

When the fluid is a gas or gas mixture, this fluid is for example air, neutral carrier gases such as nitrogen or argon.

These fluids may come notably from industry such as for example the petroleum, plastics, paint, dye industry.

Under preferential conditions of use of a kit according to the invention, the method described above comprises a step consisting of adding to a closed container provided with zones (optical windows) enabling optical detection by a suitable apparatus, and openings for the circulation or addition of liquids or gases, said container containing in separate compartments, a reagent capable of generating a stained product and an oxidant product in solid form.

As such, it is possible to add the basic solution to the solid constituents and mix all the reagents, to obtain a ready-to-use solution.

In one particular embodiment of the kit, the container is equipped with a removable separation providing two juxtaposed compartments wherein are placed in one, the reagent capable of generating a stained product and in the other the oxidant compound, in solid form, the removable separation is removed, and a basic solution is added to obtain the liquid reagent composition for detecting phenol or phenol derivatives according to the invention.

If for the use of the method above, a large quantity of reagent composition is used, the method may be used for the selective depollution of phenol and its derivatives, in particular when phenol or its derivatives are located in a gaseous fluid.

For this reason, the present application equally relates to a method for the selective depollution of phenol or its derivatives, characterized in that a fluid containing phenol or one of the compounds thereof is contacted with a reagent composition defined above. The fluid is in particular a gaseous fluid.

The preferential conditions of use of the liquid reagent compositions described above, choice of preferential reagents, proportions, etc. also apply to the other subject matter of the invention mentioned above, notably to the methods or kits.

The following examples illustrate the present application and the invention will be understood more clearly with reference to the appended drawings wherein FIG. 1 (FIG. 3) is a UV/Visible absorption tracking curve of the formation of a stained product by bubbling phenol contained in a liquid in a reagent composition according to the present invention.

EXAMPLE 1

Reagent Composition for Detecting Phenol or Phenol Derivatives 2.4 mL of a 0.016 M borate buffer solution at pH 9 is added into a pre-mixing vessel where the reagents are present in quantities such that, after mixing, the concentrations of reagent capable of generating a stained product AAP and of oxidant potassium hexacyanoferrate are both equal to $8.0.10^{-4}$ M.

A ready-to-use liquid reagent composition suitable for use for assaying phenol or phenol derivatives is thus obtained. This reagent composition may produce in the presence of phenol or phenol derivative a stained quinoid compound having for phenol an absorption peak close to 510 nm. The composition has a pH equal to 9.

EXAMPLE 2

Reagent Composition for Detecting Phenol or Phenol Derivatives 2.4 mL of a 0.016 M borate buffer solution at pH 9 is added into a vessel where the reagents are present in quantities such that, after mixing, the concentrations of AAP and potassium hexacyanoferrate are both equal to $1.6.10^{-2}$ M and $8.0.10^{-4}$ M, respectively.

A ready-to-use liquid reagent composition suitable for use for assaying phenol or phenol derivatives is thus obtained. This reagent composition may produce in the presence of phenol or phenol derivative a stained quinoid compound having for phenol an absorption peak close to 510 nm. The composition has a pH equal to 9.

EXAMPLE 3

Detection of Phenol and Phenol Derivatives in a Liquid Mixture 0.6 mL of $10^{-4}$ M phenol is added into a vessel containing the ready-to-use reagent for detecting phenol or phenol derivatives from example 1.

Figure 1:
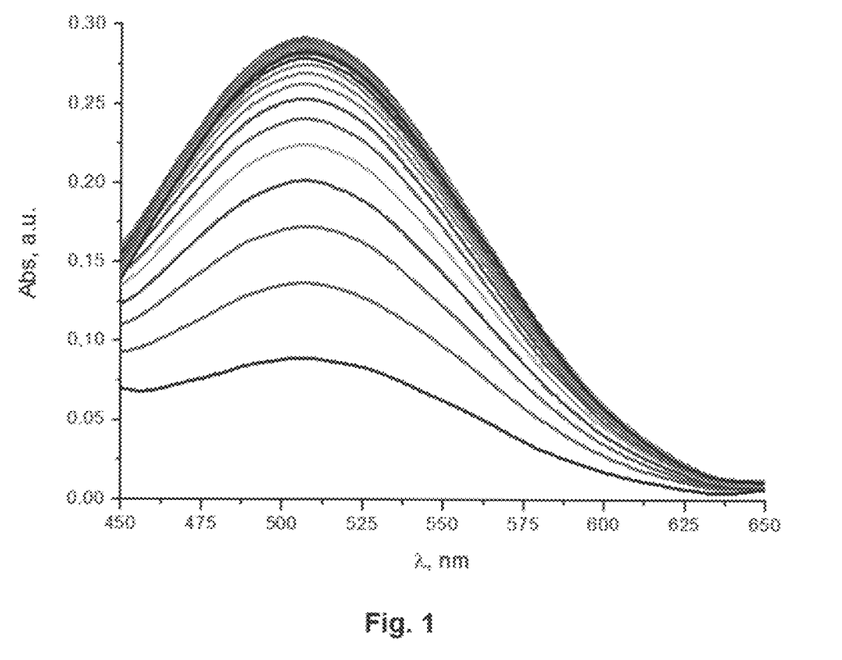
Figure 2:
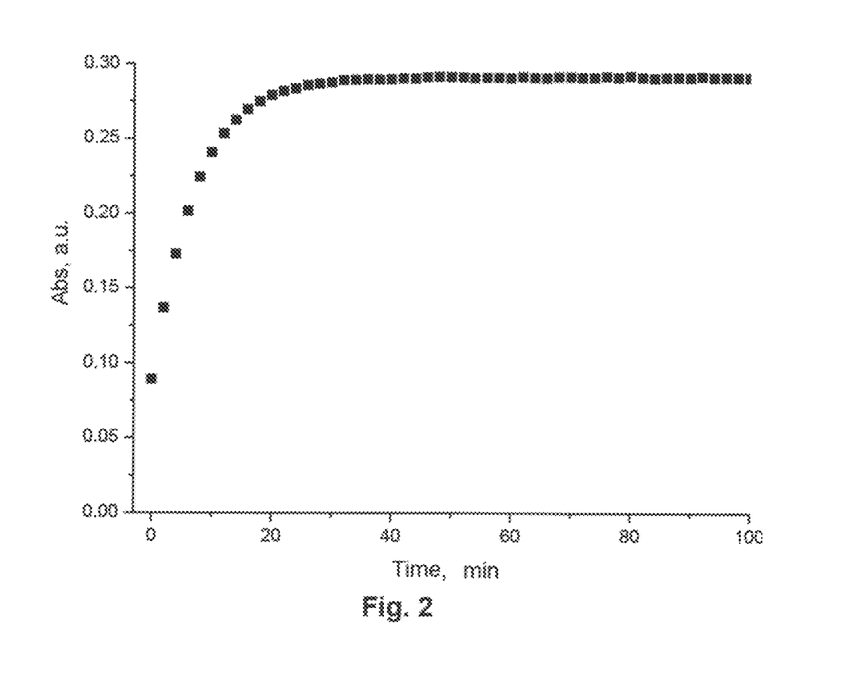
FIG. 2 (FIG. 4) represents a curve for tracking the progression of absorbance over time at 506 nm due to the formation of stained product by bubbling phenol contained in a liquid in a reagent composition according to the present invention over time.

UV-Visible absorption spectroscopy tracking over time makes it possible to observe the appearance of a peak at 506 nm, characteristic of the reaction product between the reagent capable of generating a stained product and phenol in the presence of the oxidant. The intensity of this peak increases as exposure progresses and then remains stable, meaning that phenol is progressively used up by the reaction, and that the quantity of quinoid stained product resulting from the reaction remains stable. The corresponding curve is shown in FIG. 1 (original FIG. 3). The stability of the staining obtained is also observed with the plateau in FIG. 2 (original 4). As such, the detection of phenol in a liquid mixture is possible, and may further be qualitative or quantitative.

EXAMLE 4

Detection of Phenol is a Gas Mixture

A 100 mL/min continuous gas stream containing a fixed concentration of 950 ppb of phenol was bubbled in a vessel containing the ready-to-use reagent composition for detecting phenol or phenol derivative in example 2. The gas stream is supplied directly into the measuring vessel via a tube a few mm in diameter at the end whereof a syringe needle is fitted which is kept in the liquid. The needle is positioned such that the bubbles do not enter the optical path during measurement.

Figure 3:
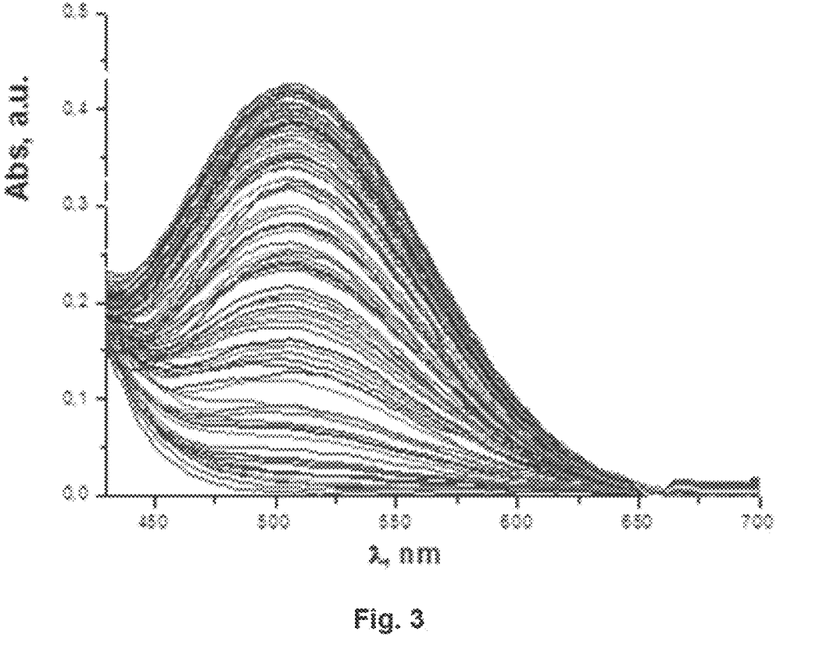
FIG. 3 (FIG. 6) is a UV/Visible absorption tracking curve of the formation of a stained product by bubbling phenol contained in a gas in a reagent composition according to the present invention.
Figure 4:
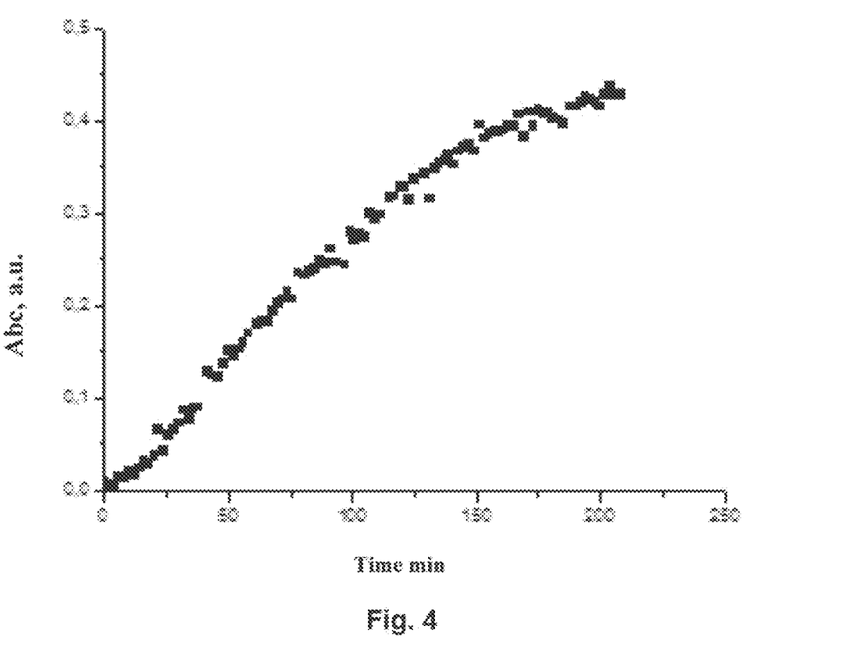
FIG. 4 (FIG. 7) represents a curve for tracking the progression of absorbance over time at 506 nm due to the formation of stained product by bubbling phenol contained in a gas in a reagent composition according to the present invention over time.

A deuterium-halogen source (Ocean Optics, DH-2000-BAL) lights up the vessel and the absorption spectra are recorded by a UV-Visible spectrophotometer (Ocean Optics, QE65000). Absorbance tracking as a function of time makes it possible to observe the appearance of a peak at 506 nm, characteristic of the reaction product between the reagent capable of generating a stained product and phenol in the presence of the oxidant. The intensity of this peak increases as exposure progresses and then starts to stabilise, meaning that the probe molecule is progressively used up by the reaction. The results obtained are shown in FIGS. 3 and 4, respectively.

This absorbance property of the solution may be correlated with the concentration of phenol by means of a calibration curve. With the absorbance is associated a change of colour of the solution visible to the naked eye. As such, the detection of phenol in a gas mixture is possible, and may further be qualitative or quantitative.

Experiment 1: Calibration Curve of Phenol in a Liquid Mixture

Figure 5:
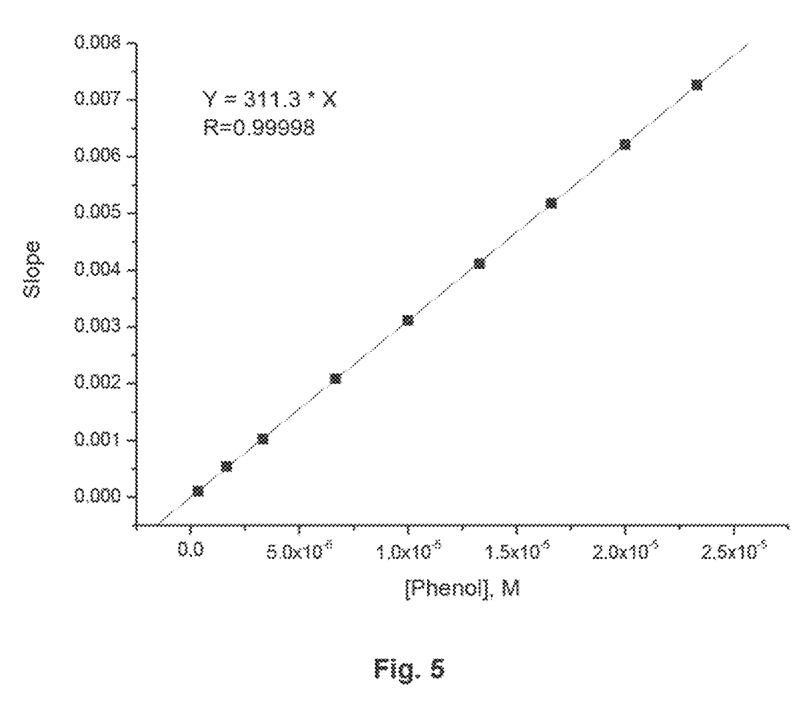
FIG. 5 (FIG. 8) represents a calibration curve for the detection of phenol in a liquid.

The same method as in example 3 was repeated for different phenol concentrations. The rate of formation of the stained reaction product between phenol and the reagents of the reagent composition of example 1 is dependent on the phenol concentration in solution. As such, plotting the value of the slopes as a function of the concentration gives the calibration curve for phenol detection. The calibration curve is reproduced in FIG. 5.

Consequently, the slope obtained is correlated with the phenol concentration and it is possible using this curve to determine the concentration of a mixture containing an unknown quantity of phenol.

Experiment 2: Calibration Curve of Phenol in a Gas Mixture

Figure 6:
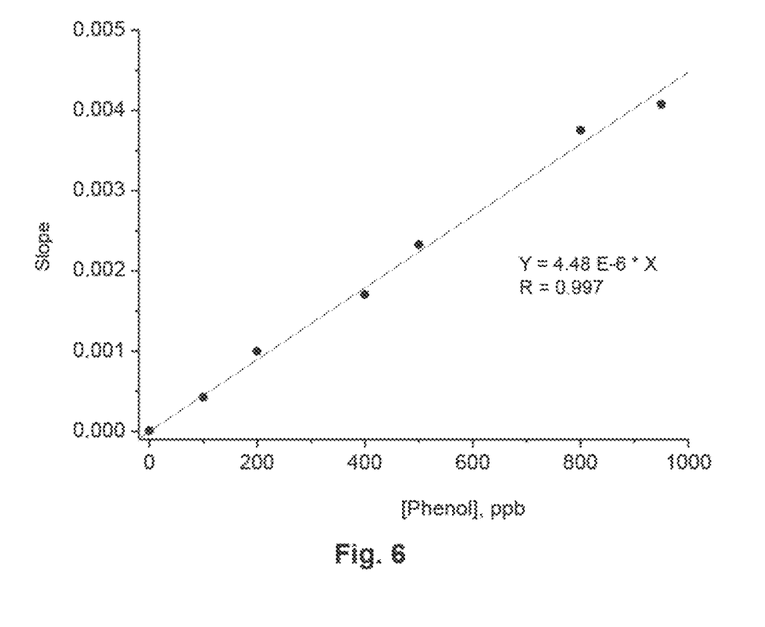
FIG. 6 represents a calibration curve for the detection of phenol in a gas.

The same method as in example 4 is repeated for different phenol concentrations. The rate of formation of the reaction product between phenol and the reagents is dependent on the phenol concentration in solution. As such, plotting the value of the slopes as a function of the concentration gives the calibration curve for phenol detection (FIG. 6).

Consequently, the slope obtained is correlated with the phenol concentration and it is possible using this curve to determine the concentration of a mixture containing an unknown quantity of phenol.

EXAMPLE 4

Two-Compartment Kit

Figure 7:
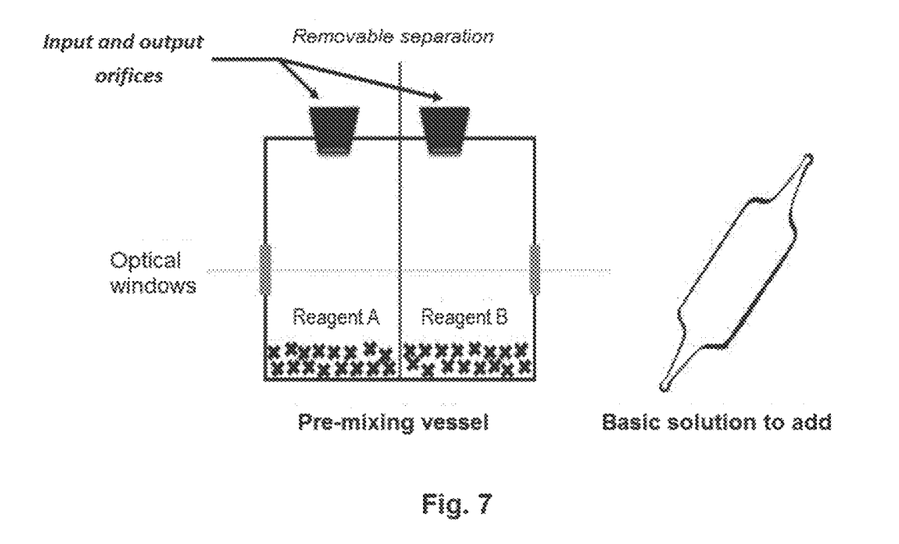
FIG. 7 represents an embodiment of a kit according to the invention.

FIG. 7 represents an embodiment of a kit according to the invention comprising a closed container provided with zones (optical windows) enabling optical detection by a suitable apparatus, and openings for the circulation or addition of liquids or gases.

The container is equipped with a removable separation providing two juxtaposed compartments wherein are placed in one, the reagent capable of generating a stained product and in the other the oxidant compound, in solid form. The mixture of these two products can be made by removing the removable separation.

It is possible to add a basic solution prepared in advance contained in a suitable container, in this case an ampoule, to the solid constituents and mix all the reagents, to obtain a ready-to-use solution.

The detection of phenol or a phenol derivative in a liquid fluid may be performed for example directly via the openings of the container. Bubbling a gas mixture containing phenol is possible directly in the container.

Detection may be performed directly by connecting an optical detection system to the optical windows of the container.

The invention claimed is:

1. A liquid reagent composition for detecting phenol or phenol derivatives comprising:
   a reagent capable of generating a stained product by forming a bond with phenol or a phenol derivative,
   an oxidant compound or mixture of oxidant compounds,
   a basic compound or mixture of basic compounds,
   wherein the ratio of [reagent capable of generating a stained product] : [oxidant compound or mixture of oxidant compounds] is 1:2 to 50:1, and
   wherein the liquid reagent has a pH greater than 7.

2. The liquid reagent composition according to claim 1, wherein the reagent capable of generating a stained product is 4-aminoantipyrine (AAP) or a derivative of AAP having formula I formula I where: R1 is an alkyl radical containing 1 to 30 carbon atoms, linear or branched, or an aryl radical; R2 is a phenyl or para-aminophenyl radical; R3 is an alkyl radical containing 1 to 30 carbon atoms, linear or branched.

3. The liquid reagent composition according to claim 1, wherein the oxidant compound or oxidant compounds are selected from the group consisting of potassium persulphate, potassium peroxomonosulphate; hydrogen peroxide and potassium hexacyanoferrate.

4. The liquid reagent composition according to claim 1, wherein the basic compound or mixture of basic compounds comprising a buffer solution selected from the group consisting of phosphate, 2-amino-2-(hydroxymethyl)-1,3-propanediol, carbonate, glycine-sodium hydroxide, and borate buffer, to obtain a basic pH.

5. The liquid reagent composition according to claim 1, wherein
   the reagent capable of generating a stained product is AAP,
   the basic compound or mixture of basic compounds is chosen among a phosphate buffer or a borate buffer, and
   the oxidant compound or oxidant compounds is potassium hexacyanoferrate or a mixture of potassium hexacyanoferrate and one or a plurality of further oxidant compounds.

6. The liquid reagent composition according to claim 1, wherein the ratio of [reagent capable of generating a stained product] : [oxidant compound or mixture of oxidant compounds] is 1:2 to 10:1.

7. The liquid reagent composition according to claim 1, wherein the reagent capable of generating a stained product by forming a bond with phenol or a phenol derivative and the oxidant compound or mixture of oxidant compounds are present in quantities such that, after mixing, the concentrations of reagent capable of generating a stained product are equal to $1.0 \cdot 10^{-3}$ M to $5.10^{-5}$ M.

8. The liquid reagent composition according to claim 1, wherein the reagent capable of generating a stained product by forming a bond with phenol or a phenol derivative and the oxidant compound or mixture of oxidant compounds are present in quantities such that, after mixing, the concentrations of oxidant are equal to: $2.0 \cdot 10^{-3}$ M to $2.10^{-6}$ M.

9. The liquid reagent composition according to claim 1, wherein the reagent capable of generating a stained product is 4-aminoantipyrine (AAP) or a derivative of AAP having formula I formula I where: R1 is an alkyl radical containing 1 to 30 carbon atoms, linear or branched, or an aryl radical; R2 is a phenyl or para-aminophenyl radical; R3 is substituted phenyl.

* * * * *